US010054528B2

(12) United States Patent
Ling et al.

(10) Patent No.: US 10,054,528 B2
(45) Date of Patent: Aug. 21, 2018

(54) METHOD FOR DEMONSTRATING THE CAPABILITY OF STRENGTHENING SCALP AND/OR PREVENTING DANDRUFF

(71) Applicant: Conopco, Inc., Englewood Cliffs, NJ (US)

(72) Inventors: Zihui Ling, Shanghai (CN); Xiaoying Bian, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 197 days.

(21) Appl. No.: 15/038,062

(22) PCT Filed: Nov. 10, 2014

(86) PCT No.: PCT/EP2014/074142
§ 371 (c)(1),
(2) Date: May 20, 2016

(87) PCT Pub. No.: WO2015/078686
PCT Pub. Date: Jun. 4, 2015

(65) Prior Publication Data
US 2016/0305860 A1    Oct. 20, 2016

(30) Foreign Application Priority Data

Nov. 29, 2013  (WO) ................ PCT/CN2013/088221
Jan. 14, 2014  (EP) .................................... 14151028

(51) Int. Cl.
*C12Q 1/02* (2006.01)
*G01N 3/56* (2006.01)
*G01N 3/24* (2006.01)

(52) U.S. Cl.
CPC .............. *G01N 3/56* (2013.01); *C12Q 1/025* (2013.01); *G01N 3/24* (2013.01); *G01N 2203/0298* (2013.01); *G01N 2333/375* (2013.01)

(58) Field of Classification Search
CPC ........... C12Q 1/025; G01N 2203/0298; G01N 2333/375; G01N 3/24; G01N 3/56
See application file for complete search history.

(56) References Cited

U.S. PATENT DOCUMENTS

| 4,151,304 | A | 4/1979 | Evans |
| 4,373,382 | A | 2/1983 | Brun |
| 7,240,539 | B2 | 6/2007 | Massaro et al. |
| 7,632,633 | B2 | 12/2009 | Iwai et al. |
| 7,862,507 | B2 | 1/2011 | Crowther et al. |
| 8,182,425 | B2 | 5/2012 | Stamatas et al. |
| 2004/0185430 | A1 | 9/2004 | Lefebvre et al. |
| 2006/0130564 | A1 | 6/2006 | Massaro et al. |
| 2007/0054261 | A1 | 3/2007 | Sherman et al. |
| 2009/0186408 | A1* | 7/2009 | Wang ................... C12N 5/0068 435/373 |
| 2011/0300572 | A1* | 12/2011 | Dueva-Koganov .... G01N 33/15 435/29 |
| 2012/0040003 | A1* | 2/2012 | Yarovoy .............. A61K 8/4933 424/489 |
| 2012/0324984 | A1 | 12/2012 | Wakefield et al. |

FOREIGN PATENT DOCUMENTS

| JP | 2002112970 | 4/2002 |
| JP | 2009268501 | 11/2009 |
| JP | 2013081787 | 5/2013 |
| KR | 20090053478 | 5/2009 |
| WO | WO2005065551 | 7/2005 |
| WO | WO2012020043 | 2/2012 |
| WO | WO2013007019 | 1/2013 |
| WO | WO2015007502 | 1/2015 |

OTHER PUBLICATIONS

Bhushan et al., "Surface, Tribological, and Mechanical Characterization of Synthetic Skins for Tribological Applications in Cosmetic Science", Journal of Applied Polymer Science, 2011, vol. 120, No. 5, pp. 2881-2890; XP055122523. pp. 1 to 10.
Bhushan, "Nanotribological and nanomechanical properties of skin with and without cream tratment using atomic force microscopy and nanoidentation", Journal of Colloid and Interface Science, 2012, vol. 367, Issue 1, pp. 1-33; XP028393696. pp. 11 to 43.
IPRP2 in PCTEP2014074142 dated Feb. 17, 2016. p. 44 to 58.
Gerhardt et al., "Fabrication, Characterisation and Tribological Investigation of Artificial Skin Surface Lipid Films", Tribology Letters, 2009, vol. 34, No. 2, pp. 81-93; XP019689803. pp. 59 to 71.
Search Report and Written Opinion in EP14151028 dated Jun. 27, 2014. pp. 1 to 6.
Search Report and Written Opinion in PCTEP2014074142 dated Jan. 19, 2015. pp. 7 to 15.

* cited by examiner

*Primary Examiner* — Jennifer Wecker
(74) *Attorney, Agent, or Firm* — Karen E. Klumas

(57) ABSTRACT

Disclosed is a method for demonstrating the capability of strengthening scalp and/or preventing dandruff of a personal care product or component thereof, the method comprising selecting a first portion of a solid porous article of non-animal origin, treating the first portion of the article with the personal care product or the component thereof, subjecting the treated first portion to a drying step and mechanically treating the dried first portion.

15 Claims, No Drawings

METHOD FOR DEMONSTRATING THE CAPABILITY OF STRENGTHENING SCALP AND/OR PREVENTING DANDRUFF

FIELD OF THE INVENTION

The present invention relates to a method for demonstrating the capability of strengthening scalp and/or preventing dandruff of a personal care product or component thereof. In particular, the method comprises selecting a first portion of a solid porous article of non-animal origin, treating the first portion of the article with the personal care product or the component thereof, subjecting the treated first portion to a drying step and mechanically treating the dried first portion.

BACKGROUND OF THE INVENTION

Personal care products have been designed to improve the condition of skin or hair. Unfortunately, however, some benefits, for example scalp strengthening of such products may not be immediately perceived by a user and in fact may take many hours or even days of repeat application to yield consumer-perceivable benefits.

WO 2012/020043 A1 (Unilever) discloses an apparatus for analyzing the condition of skin, scalp or hair of a user, comprising a transducer device responsive to a property of the skin, scalp or hair providing an analog output related to the property, a serial device for outputting a digital signal from an audio signal input, wherein the audio signal is generated from the transducer analog output related to the property, and wherein the serial device provides data packet transmission sufficient for an application to find both a point at which a new packet begins and an opportunity to interpret its received raw data signal.

However, the instrumental measurements to evaluate the condition of scalp may be complicated and/or involve expensive laboratory equipment. Furthermore such measurements often result in numerical parameters that are difficult for laymen to understand or at least relate to the expected product efficacy.

The present inventors have thus identified a need to provide methods which can demonstrate the ability of strengthening scalp and/or preventing dandruff but which does not need specialist equipment and/or is easily related to consumer benefits.

SUMMARY OF THE INVENTION

In a first aspect the present invention provides a method for demonstrating the capability of strengthening scalp and/or preventing dandruff of a personal care product or component thereof, the method comprising:

(i) selecting a first portion of a solid porous article of non-animal origin;
(ii) treating the first portion of the article with the personal care product or the component thereof;
(iii) subjecting the treated first portion to a drying step; and
(iv) mechanically treating the dried first portion.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the product, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

The method of the present invention comprises step (i) of selecting a first portion of a solid porous article of non-animal origin. Non-animal origin as used herein means that the article is not derived from animal. It should be noted that animal includes human being. Porous article means any article having pore on surface and/or void in body. Solid refers to the state at ambient environment (25° C. and atmospheric pressure).

Preferably, the article comprises artificial skin, polyurethane, cellulose, polysaccharide, plant tissue, food made by flour, paper, sponge, or a combination thereof. The plant tissue may be an entire plant, flowers, leaves, petals, stems, fruits, seeds or roots, and/or the fragments thereof. The food made by flour may be selected from bread, cake, wafer, cookie, potato chip, cereal, or combination thereof. More preferably, the article comprises artificial skin, plant leaf, plant petal, fruit skin, bread, fungi [especially jelly fungi (Auriculariales)], or a combination thereof as they are thin but with a large surface area and therefore dry relatively quickly. Even more preferably the article comprises artificial skin, jelly fungi (Auriculariales) and bread. Most preferred article includes artificial skin and jelly fungi (Auriculariales) because they are fragile when undergoing mechanically interaction.

To be visible to naked eye and/or prone to mechanical treatment, the length of the first portion of the article is preferably from 1 mm to 10 m, more preferably from 5 mm to 2 m, even more preferably from 1 cm to 60 cm, and most preferably from 2 cm to 30 cm. Herein the length refers to the longest distance of any point of the first portion of the article.

Meanwhile, to effectively absorb the personal care product or component thereof, the article preferably has a pore size of from 10 nm to 2 mm, more preferably from 100 nm to 500 microns, even more preferably from 500 nm to 200 microns. The pore size refers to the largest measureable distance of the pore along the largest surface of the article in the event that the pore is not well-defined sphere. It may be measured for example by scanning electron microscopy (SEM). The value of the pore size is obtained as number average value of at least ten pores.

The method of the present invention comprises step (ii) of treating the first portion of the article with the personal care product or the component thereof.

The treatment comprises at least contacting the first portion with the product or component. The contact may, for example, comprise spreading the product or component on at least one surface of the first portion. Additionally or alternatively the contact may comprise soaking the first portion in a liquid comprising the product or component.

The treatment may also comprise rinsing the first portion following contact with the product or component.

The duration of the treatment step (ii), i.e., the time between starting to apply the personal care product or component to the article and commencement of the drying step (iii), is preferably between 1 s and 24 hours. However, the method may be especially suitable for situations where rapid demonstration of product efficacy is desired, such as for example, in-store and/or at point of sale. Thus it is preferred that the duration of the treatment step is less than 2 hours, more preferably less than 1 hour, more preferably still less than 30 minutes and most preferably less than 10 minutes. However, to show the difference effectively, the duration of the treatment step is more preferably at least 10 s, and even more preferably at least 30 s.

The personal care product is preferably one intended for application to the hair and/or skin for the purpose of improving the condition thereof. In particular the product is preferably intended to improve a condition of hair and/or skin selected from scalp strengthening, nourishment, barrier function, moisture retention, resilience, anti-dandruff, and combinations thereof. Preferably the product is a hair care product, especially a hair care product intended to improve the condition of the scalp.

In a preferred embodiment the first portion is treated with a component of the personal care product in step (ii). Treating the portion with the component rather than the entire product allows, for example, the component to be applied to the portion in a higher concentration than in the product and/or to be applied in a different manner than would be achieved by applying the whole product. Thus the capability of strengthening scalp and/or preventing dandruff of the component can be enhanced such that the same may be demonstrated in a short time. Preferably the first portion of the article is treated with an aqueous liquid comprising the component. More preferably the concentration of the component by weight of the aqueous liquid is greater than the concentration of the component by weight of the personal care product. For example the concentration of the component by weight of the aqueous liquid may be at least twice, more preferably at least three times, more preferably still at least five times and most preferably at least ten times the concentration of the component by weight of the personal care product.

The component should be associated with the product in some manner. By "associated" is meant that the method preferably comprises a step of identifying the component as an ingredient of the product. For example, prior to step (i) the method may comprise a step of selecting a component of the personal care product for assessment. Additionally or alternatively, the method may comprise a step of communicating the component as an ingredient of the personal care product through indicia such as text, video, audio and the like.

The component should be selected to be a component which may provide scalp strengthening, nourishment, barrier function, moisture retention, anti-dandruff or combinations thereof. For example the component preferably is or at least comprises a humectant, emollient, bioactive or combination thereof. For sake of clarity, typically the component is not water. More preferably the component comprises or is polyhydric alcohol, fatty materials (such as oils, fatty alcohols, fatty acids and/or soaps), ester emollient, hydrocarbon emollient, silicone oil, vitamin, amino acid, plant extract, or a mixture thereof. Most preferably, the component comprises polyhydric alcohol Preferred polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. Most preferred is glycerol (also known as glycerin).

Silicone oils may be divided into the volatile and nonvolatile variety. The term "volatile" as used herein refers to those materials which have a measurable vapor pressure at ambient temperature (25° C.). Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-5}$ to about $4 \times 10^{-4}$ m$^2$/s at 25° C.

Organopolysiloxane crosspolymers can be usefully employed. Representative of these materials are dimethicone/vinyl dimethicone crosspolymers and dimethicone crosspolymers available from a variety of suppliers including Dow Corning (9040, 9041, 9045, 9506 and 9509), General Electric (SFE 839), Shin Etsu (KSG-15, 16 and 18 [dimethicone/phenyl vinyl dimethicone crosspolymer]), and Grant Industries (Gransil brand of materials), and lauryl dimethicone/vinyl dimethicone crosspolymers supplied by Shin Etsu (e.g. KSG-31, KSG-32, KSG-41, KSG-42, KSG-43 and KSG-44).

Specific examples of fatty materials include stearyl alcohol, glyceryl monoricinoleate, mink oil, cetyl alcohol, isopropyl isostearate, stearic acid, isobutyl palmitate, isocetyl stearate, oeyl alcohol, isopropyl laurate, hexyl laurate, decyl oleate, octadecan-2-ol, isocetyl alcohol, eicosanyl alcohol, behenyl alcohol, cetyl palmitate, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate, and mixtures thereof.

Among the ester emollients are:
a) Alkenyl or alkyl esters of fatty acids having 10 to 20 carbon atoms. Examples thereof include isoarachidyl neopentanoate, isodecyl neopentanoate, isononyl isonanoate, cetyl ricinoleate, oeyl myristate, oeyl stearate, and oeyl oleate.
b) Ether-esters such as fatty acid esters of ethoxylated fatty alcohols.
c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. Exemplative is pentaerythrityl tetraethylhexanoate.

d) Wax esters such as beeswax, spermaceti wax and tribehenin wax.

e) Sterols esters, of which cholesterol fatty acid esters are examples thereof.

f) Sugar ester of fatty acids such as sucrose polybehenate and sucrose polycottonseedate.

Hydrocarbons which are useful include petrolatum, mineral oil, $C_{11}$-$C_{13}$ isoparaffins, polyalphaolefins, and especially isohexadecane.

Vitamins may be lipid-soluble vitamins and water-soluble vitamins but preferably vitamins are water soluble. "Water soluble vitamins" as used herein refers to vitamins that dissolve in water to give a solution with a concentration of at least 1 gram per liter at 25° C. Exemplary water-soluble vitamins include ascorbic acid (vitamin C), thiamin (vitamin $B_1$) niacin (nicotinic acid), niacinamide (vitamin $B_3$), riboflavin (vitamin $B_2$), pantothenic acid (vitamin $B_5$), biotin, folic acid, pyridoxine (vitamin $B_6$), and cyanocobalamin (vitamin B12).

Examples of suitable amino acids include arginine, cysteine, glutamine, glutamic acid, isoleucine, leucine, methionine, serine and valine, and/or precursors and derivatives thereof.

The method of the present invention comprises step (iii) of subjecting the treated first portion to a drying step.

The drying step (iii) may comprise contacting the treated first portion with hot air, leaving the first portion in ambient air, vacuum drying the first portion, ironing the first portion or a combination thereof. Ambient as used herein means at environmentally temperature, often 25° C., and at atmospheric pressure. Hot air as used herein refers to air having temperature higher than 25° C. It is preferred that the way of drying comprises contacting the treated first portion with hot air, leaving the treated first portion in ambient air or combination thereof. Contacting the treated first portion with hot air preferably includes placing the treated first portion into oven and/or blowing the treated first portion with a drier. In certain embodiments, it is preferred that the drying step is conducted under atmospheric pressure.

To provide even more rapid drying and/or be convenient to operate it is preferred that the drying temperature is from −50 to 300° C., more preferably from 0 to 200° C., even more preferably from 25 to 150° C. and most preferably from 40 to 100° C. The duration of the drying step is typically from 1 second and 200 hours, more preferably from 1 minute to 50 hours, even more preferably from 5 minutes to 20 hours, and most preferably from 15 minutes to 6 hour.

When the way of drying comprises contacting the treated first portion with hot air, the duration of the drying step is preferably at least 1 second, more preferably at least 10 seconds, even more preferably from 2 minute to 10 hours, still even more preferably from 2 minutes to 5 hours, most preferably from 10 minutes to 2 hour. The hot air preferably has a temperature of 30 to 200° C., more preferably from 35 to 120° C., and even more preferably from 35 to 80° C., most preferably from 40 to 60° C.

When the way of drying naturally at ambient environment is employed, the duration of the drying step is preferably at least 1 hour, more preferably at least 5 hours, even more preferably from 10 to 100 hours.

The method of the present invention comprises step (iv) of mechanically treating the dried first portion. Preferably, the mechanical treatment comprising the step of applying a force of at least 50 µN, more preferably from 500 µN to 100 N, even more preferably from 5 mN to 10 N, most preferably from 50 mN to 4 N. The force is preferably a normal force.

Preferably, the way of mechanical treatment comprises combing, scratching, folding, tearing, kneading or a combination thereof, more preferably combing folding kneading or a combination thereof. The even more preferred mechanical treatment comprises combing, folding or a combination thereof. Where the combing is employed, any comb for human being and/or animal may be used. It is preferred that combing is conducted by an ordinary comb for human being. Where the mechanical treatment comprises a folding step, it is preferred that the mechanical treatment also comprises an unfolding step.

Following step (iv), the method may comprise a step (v) of assessing at least one attribute of the treated first portion. Preferably the attribute assessed is appearance, such as size, shape, surface texture, colour, marks, integrity, transparency or a combination thereof. Preferably, the appearance is assessed via observing by human naked eye directly. Additionally or alternatively, the appearance is assessed by taking images and/or videos with magnification of no greater than 100 times, preferably less than 10 times. Integrity could include the presence/amount of flakes. Additionally or alternatively, the attribute assessed is weight.

The method of the present invention is particular effective when used to evaluate the capability of strengthening scalp and/or preventing dandruff of the personal care product or the component relative to a placebo product. Thus in a most preferred embodiment the method comprises selecting a second portion of the article in step (i); treating the second portion with a placebo product in step (ii); treating the second treated portion to the drying step (iii), and the second dried portion is also mechanically treated in step (iv).

The second portion should be substantially identical to the first portion, for example in respect of the type of the article as well as length and pore size.

Placebo as used herein means product which have no or lower levels of component than that of the personal care product or component to be tested. The placebo may be any composition different from the personal care product or component to be tested. However, it is preferred that the concentration of the component by weight of the placebo product is no greater than half (½), more preferably one quarter (¼), and most preferably one tenth (1/10) of the concentration of the component by weight of the personal care product or component to be tested. Most preferably the placebo is water (or at least comprises at least 99% water by weight of the placebo product, more preferably 99.9 to 100%).

The assessed attribute in step (v) is preferably a change in a characteristic of the treated first portion relative to untreated article and/or relative to the treated second portion. The characteristic is preferably appearance and/or weight, more preferably marks, integrity and/or weight.

The following examples are provided to facilitate an understanding of the invention. The examples are not intended to limit the scope of the claims.

EXAMPLES

Example 1

A test sample was prepared by mixing 8 g of glycerine, 0.48 g of sunflower oil and 31.52 g of water. The placebo was 40 g of water. One piece of artificial skin (3 cm×3 cm, VITRO-SKIN® IMS Inc. USA) was placed into the test sample and another identical piece was placed into the placebo. After soaking for 10 minutes, the two pieces of artificial skin were removed from the test sample and placebo, spread apart in two identical plates, and placed under ambient environment (atmospheric pressure, 25° C., and 50% of relative humidity) for 16 hours. Then, these two pieces of artificial skin were folded and unfolded once by human hand.

It was observed that the piece of artificial skin treated by the placebo had been broken into a few pieces, showing that the artificial skin was fragile. However, it was found that the piece treated by the test sample remained intact, demonstrating the strengthening of artificial skin.

Example 2

The preparation of test sample, placebo, and the soaking process was identical with that in Example 1. Then these two pieces of artificial skin was dried under ambient environment (atmospheric pressure, 25° C., and 50% of relative humidity) for 48 hours and were scratched 20 times each using a metal comb with similar force to mimic scalp/hair combing.

It was observed that there were very clear scratch marks on the artificial skin treated by placebo, and flakes had fallen off from the artificial skin treated by placebo, manifesting that it was brittle. In contrast, there was no noticeable scratch mark and flake on the artificial skin treated by the test sample, showing the strengthening of artificial skin.

Example 3

The test and findings were similar with that of Example 2 except that the drying step was conducted at 50° C. in oven for 2 hours.

Example 4

Test sample 1 (s1) was prepared by mixing 20 g of glycerine, 0.4 g of sunflower oil and 19.6 g of water. Test sample 2 (s2) was prepared by mixing 20 g of CLEAR® Shampoo, and 20 g of water. The shampoo comprises 0.5% by weight of glycerine and 0.1% by weight of sunflower oil. The placebo was 40 g of water.

Three snow fungi (*Tremella fuciformis*) were placed into S1, S2, and placebo respectively. After soaking for 1 minute, they were removed from the test samples and placebo, and blown by ordinary hair drier for 5 minutes. Then, these treated snow fungi were scratched 10 times each by an ordinary comb for human use.

It was observed that the snow fungus treated by the placebo had been broken into a few pieces, showing that the fungus was fragile. In contrast, it was found that the snow fungi treated by both S1 and S2 remained intact, demonstrating the snow fungi were nourished and strengthened by both S1 and S2.

Example 5

The test and findings were identical with that of Example 2 except that two pieces of bread (8 cm×8 cm×0.8 cm) were employed instead of artificial skin.

The invention claimed is:

1. A method for demonstrating the capability of strengthening scalp and/or preventing dandruff of a personal care product or component thereof, the method comprising:
   (i) selecting a first portion of a solid porous article of non-animal origin, the solid porous article comprising artificial skin, polyurethane, fungi, sponge or a combination thereof;
   (ii) treating the first portion of the article with the personal care product or the component thereof;
   (iii) subjecting the treated first portion to a drying step;
   (iv) mechanically treating the dried first portion; and
   (v) assessing at least one attribute, visible to the naked eye, of the mechanically treated first portion,
   wherein the mechanically treating comprises combing, folding or a combination thereof, and wherein the assessed attribute is a change in the appearance of the mechanically treated first portion relative to untreated article and/or relative to a mechanically treated second portion and wherein, when the assessed attribute is a change in the appearance of the mechanically treated first portion relative to a mechanically treated second portion, the mechanically treated second portion is produced by selecting a second portion of the solid porous article, treating the second portion with a placebo product, subjecting the placebo product treated portion to a drying step as in step (iii), and mechanically treating the dried placebo product treated second portion as in step (iv).

2. The method according to claim 1 wherein the length of the first portion of the article is from 2 cm to 60 cm.

3. The method according to claim 1 wherein the article has a pore size of from 100 nm to 500 microns.

4. The method accord to claim 1 wherein the method is for demonstrating the capability of strengthening scalp and/or preventing dandruff of the component of the personal care product and wherein in step (ii) the first portion of the article is treated with an aqueous liquid comprising the component.

5. The method according to claim 4, wherein the concentration of the component by weight of the aqueous liquid is greater than the concentration of the component by weight of the personal care product.

6. The method according to claim 1 wherein the duration of the treatment step (ii) is between 10 s and 24 hours.

7. The method according to claim 1 wherein the duration of the drying step (iii) is from 5 minutes to 20 hours.

8. The method according to claim 1 wherein the drying step (iii) comprises contacting the treated first portion with hot air, leaving the treated first portion in ambient air or combination thereof.

9. The method according to claim 8 wherein drying comprises contacting the treated first portion with hot air and the hot air has a temperature of 35 to 120° C.

10. The method according to claim 1 wherein the product is a hair care product.

11. The method according to claim 1 wherein the component comprises or is polyhydric alcohol, fatty materials, ester emollient, hydrocarbon emollient, silicone oil, vitamin, amino acid, plant extract, or a mixture thereof.

12. The method according to claim 1 wherein the second portion of the article is selected in step (i); the second portion is treated with a placebo product in step (ii); the second treated portion is treated to the drying step (iii), and the second dried portion is also mechanically treated in step (iv).

13. The method according to claim 12, wherein the placebo is water.

14. The method according to claim 1 wherein the solid porous article comprises artificial skin.

15. The method according to claim 1 wherein the solid porous article comprises fungi.

\* \* \* \* \*